US007901687B2

(12) United States Patent
Werz et al.

(10) Patent No.: US 7,901,687 B2
(45) Date of Patent: Mar. 8, 2011

(54) **ANTIBODIES FOR THE DETECTION OF *BACILLUS ANTHRACIS* AND VACCINE AGAINST *B. ANTHRACIS* INFECTIONS**

(75) Inventors: Daniel B. Werz, Göttingen (DE); Peter H. Seeberger, Zürich (CH); Marco Tamborrini, Basel (CH); Gerd Pluschke, Bad Krozingen (DE)

(73) Assignees: Eth Zurich, Zurich (CH); Schweizerisches Tropeninstitut, Basel (CH)

( * ) Notice: Subject to any disclaimer, the term of this patent is extended or adjusted under 35 U.S.C. 154(b) by 0 days.

(21) Appl. No.: 12/226,728

(22) PCT Filed: Apr. 27, 2007

(86) PCT No.: PCT/EP2007/054137
§ 371 (c)(1),
(2), (4) Date: Oct. 27, 2008

(87) PCT Pub. No.: WO2007/125089
PCT Pub. Date: Nov. 8, 2007

(65) Prior Publication Data
US 2009/0155299 A1    Jun. 18, 2009

(30) Foreign Application Priority Data
Jun. 29, 2006 (EP) .................................. 06116359

(51) Int. Cl.
*A61K 39/00* (2006.01)
*A61K 39/38* (2006.01)
*A61K 39/40* (2006.01)
*A61K 39/395* (2006.01)
*A61K 45/00* (2006.01)
*A61K 47/00* (2006.01)

(52) U.S. Cl. ............... 424/164.1; 424/130.1; 424/141.1; 424/150.1; 424/178.1; 424/179.1; 424/183.1; 424/246.1; 424/278.1

(58) Field of Classification Search ................ None
See application file for complete search history.

(56) References Cited

U.S. PATENT DOCUMENTS
5,861,155 A * 1/1999 Lin ........................ 424/133.1

OTHER PUBLICATIONS
Steichen et al., J. of bacterio. 2003. vol. 185(6):1903-1910.*

(Continued)

*Primary Examiner* — Mark Navarro
*Assistant Examiner* — JaNa Hines
(74) *Attorney, Agent, or Firm* — Wenderoth, Lind & Ponack, L.L.P.

(57) ABSTRACT

The present invention relates to conjugates of oligosaccharides of formula 1, wherein R is a linker to a carrier protein and optionally comprises up to three further saccharides, 5 and which are useful for vaccination, methods of synthesis of such conjugates, antibodies against this antigen, hybridoma producing monoclonal antibodies against this antigen, assays using these antibodies for the detection of *B. anthracis* spores and kits comprising these antibodies, and a vaccine for the prevention of *B. anthracis* infection comprising the conjugates of oligosaccharides of formula 1. Monoclonal antibodies 10 according to the invention selectively bind to *B. anthracis*, but not to related bacteria such as *B. subtilis*, *B. cereus* and other bacteria of this group such as *B. thuringiensis*.

4 Claims, 3 Drawing Sheets

OTHER PUBLICATIONS

Saskena et al. (Carbohydrate Res. 2005. vol. 340. pp. 1591-1600).*

D. B. Werz et al., "Total Synthesis of Antigen *Bacillus anthracis* Tetrasaccharide-Creation of an Anthrax Vaccine Candidate", Angew. Chem. Int. Ed., vol. 44, No. 39, pp. 6315-6318, Oct. 7, 2005.

D. B. Werz et al., "Totalsynthese eines Tetrasaccharid-Antigens von *Bacillus anthracis*—Basis fur einen Impfstoff gegen Anthrax", Angew. Chem., vol. 117, pp. 6474-6476, 2005.

R. Adamo et al., "Synthesis of the β anomer of the spacer-equipped tetrasaccharide side chain of the major glycoprotein of the *Bacillus anthracis* exosporium", Carbohydrate Research, vol. 340, No. 17, pp. 2579-2582, Dec. 12, 2005.

R. Saksena et al., "Synthesis of the tetrasaccharide side chain of the major glycoprotein of the *Bacillus anthracis* exosporium", Bioorganic & Medicinal Chemistry Letters, vol. 16, No. 3, pp. 615-617, Feb. 1, 2006.

J. M. Daubenspeck et al., "Novel Oligosaccharide Side Chains of the Collagen-like Region of Bc1A, the Major Glycoprotein of the *Bacillus anthracis* Exosporium", The Journal of Biological Chemistry, vol. 279, No. 30, pp. 30945-30953, Jul. 23, 2004.

X. Ma et al., "Neoglycoconjugates from synthetic tetra- and hexasaccharides that mimic the terminus of the O-PS of *Vibrio cholerae* 0:1, serotype Inaba", Organic & Biomolecular Chemistry, vol. 1, No. 5, pp. 775-784, Mar. 7, 2003.

R. Saksena et al., "Studies toward a conjugate vaccine for anthrax. Synthesis and characterization of anthrose [4,6-dideoxy-4-(3-hydroxy-3-methylbutanamido)-2-O-methyl-D-glucopyranose] and its methyl glycosides", Carbohydrate Research, vol. 340, No. 9, pp. 1591-1600, Jul. 4, 2005.

R. Roy, "New trends in carbohydrate-based vaccines", Drug Discovery Today: Technologies, vol. 1, No. 3, pp. 327-336, Dec. 2004.

B. Kuberan et al., "Carbohydrate Based Vaccines", Current Organic Chemistry, vol. 4, No. 6, pp. 653-677, 2000.

S. Borman, "Anthrax Antigen Synthesized", Chemical and Engineering News, vol. 83, No. 40, pp. 10-11, Oct. 3, 2005.

G. Park et al., "Synthesis of biosynthetic precursors of anthrax- and cholera-related antigenic carbohydrates", Abstracts of Papers American Chemical Society, vol. 231, p. 81, Mar. 2006.

C. Steichen et al., "Identification of the Immunodominant Protein and Other Proteins of the *Bacillus anthracis* Exosporium" Journal of Bacteriology, vol. 185, No. 6, pp. 1903-1910, Mar. 2003.

J. A. Boydston et al., "Orientation within the Exosporium and Structural Stability of the Collagen-Like Glycoprotein BcIA of *Bacillus anthracis*", Journal of Bacteriology, vol. 187, No. 15, pp. 5310-5317, Aug. 2005.

A. S. Mehta et al., "Synthesis and Antigenic Analysis of the BcIA Glycoprotein Oligosaccharide from the *Bacillus anthracis* Exosporium", Chem. Eur. J., vol. 12, No. 36, pp. 9136-9149, Dec. 13, 2006.

M. Tamborrini et al., "Anti-Carbohydrate Antibodies for the Detection of Anthrax Spores", Angew. Chem. Int., vol. 45, No. 39, pp. 6581-6582, Oct. 6, 2006.

* cited by examiner

ANTIBODIES FOR THE DETECTION OF BACILLUS ANTHRACIS AND VACCINE AGAINST B. ANTHRACIS INFECTIONS

This application is a U.S. national stage of International Application No. PCT/EP2007/054137 filed Apr. 27, 2007, which claims benefit of 60/796,180 filed Apr. 28, 2006.

FIELD OF THE INVENTION

The present invention relates to antibodies for the detection of *Bacillus anthracis* spores, oligosaccharide conjugates for the preparation of such antibodies, and a vaccine for prevention *B. anthracis* infections.

BACKGROUND OF THE INVENTION

Anthrax is an infectious disease caused by the Gram-positive spore-forming soil bacterium *Bacillus anthracis*. The endospores are remarkably resistant to physical stress such as extreme temperatures, radiation, harsh chemicals, desiccation and physical damage. These properties allow them to persist in the soil for many years. The spores are highly infectious. If this durable form of the pathogen has been inhaled, it will kill most victims if treatment does not commence within 24-48 h. In Oct. 2001, several anthrax cases resulted in four deaths in the United States after the intentional release of spores through contaminated letters. In addition to the casualties, widespread panic brought the US Postal System to the brink of collapse. These cases demonstrated the danger of *B. anthracis* as a biowarfare agent to terrorize civilian populations. Intensified scrutiny of the mechanisms underlying the pathogenicity, the detection and treatment of pathogens such as *B. anthracis* was an immediate result of the attacks.

On the surface of the exosporium glycoprotein BclA of *B. anthracis* spores, a unique tetrasaccharide of formula 1b (R=H) has been discovered recently (J. M. Daubenspeck, H. Zeng, P. Chen, S. Dong, C. T. Steichen, N. R. Krishna, D. G. Pritchard, C. L. Turnbough, Jr., *J. Biol. Chem.* 2004, 279, 30945-30953.) The antigen contains an entirely novel monosaccharide at the non-reducing end that was named anthrose. Anthrose is not even found in closely related species. Thus, the tetrasaccharide is a very attractive target for the elucidation of a highly specific immune response in order to detect selectively spores of *B. anthracis* and to develop a vaccine against this serious threat. The synthesis of the tetrasaccharide has been reported by D. B. Werz, P. H. Seeberger, *Angew. Chem. Int. Ed.* 2005, 44, 6315-6318.

SUMMARY OF THE INVENTION

The present invention relates to conjugates of an oligosaccharide of formula 1, in particular of the trisaccharide of formula 1a, the tetrasaccharide of formula 1b, or the pentasaccharide of formula 1c, wherein R is a linker to a carrier protein and optionally comprises up to three further saccharides, methods of synthesis of such conjugates, antibodies against these antigens, hybridoma producing monoclonal antibodies against these antigens, assays using these antibodies for the detection of *B. anthracis* spores and kits comprising these antibodies, and a vaccine for the prevention of *B. anthracis* infection comprising the conjugates of oligosaccharide of formula 1.

BRIEF DESCRIPTION OF THE FIGURES

FIG. 1: Development of anti-carbohydrate IgG responses in mice. Mice were immunized two to four times with ImmunEasy™ (QIAGEN) formulated *B. anthracis* synthetic carbohydrates 1. Shown are mean ELISA readouts±SD obtained with serial dilution of monoclonal antibodies (mAbs) or mouse sera taken pre-immune (PRE IMM) and two weeks after the second (2.IMM), third (3.IMM) or fourth (4.IMM) immunization. X-axis in A and C: dilution of mouse sera.

A: Anti-tetrasaccharide IgG response in ELISA of immune sera after immunization with tetrasaccharide-KLH 1b (R=KLH).

B: Anti-tetrasaccharide response of tetrasaccharide specific mAbs (MTA).

C: Anti-disaccharide IgG titers of sera after immunization with disaccharide-KLH 1 (R=KLH).

Column I: bright field microscopy; column II: Cy3-specific immunofluorescence staining.

A: *B. anthracis* spores with an isotype-matched control mAb;

B: *B. anthracis* spores with a tetrasaccharide 1b specific mAb;

C: *B. cereus* spores with a tetrasaccharide 1b specific mAb.

DETAILED DESCRIPTION OF THE INVENTION

Figure 1:
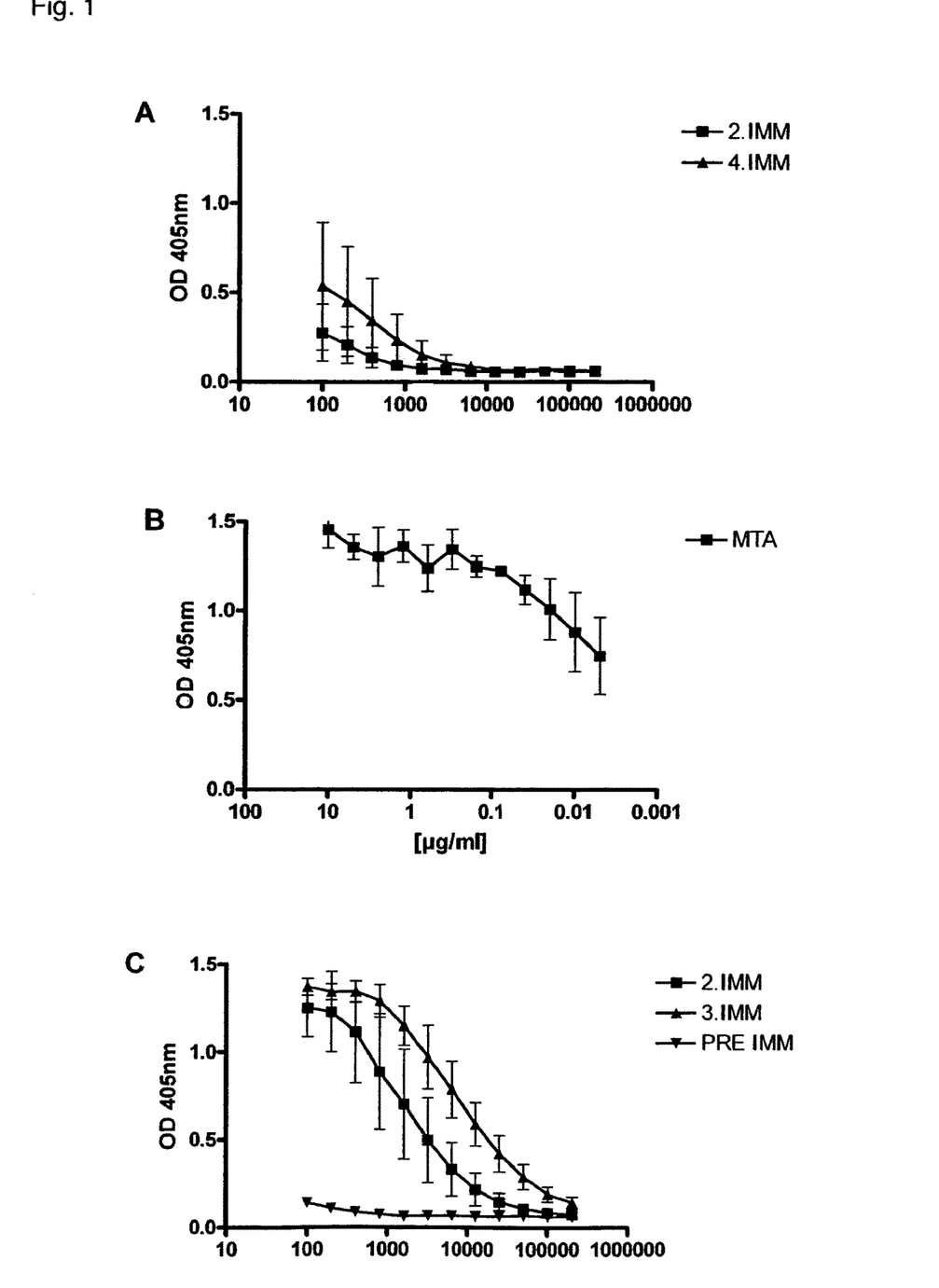
Figure 2:
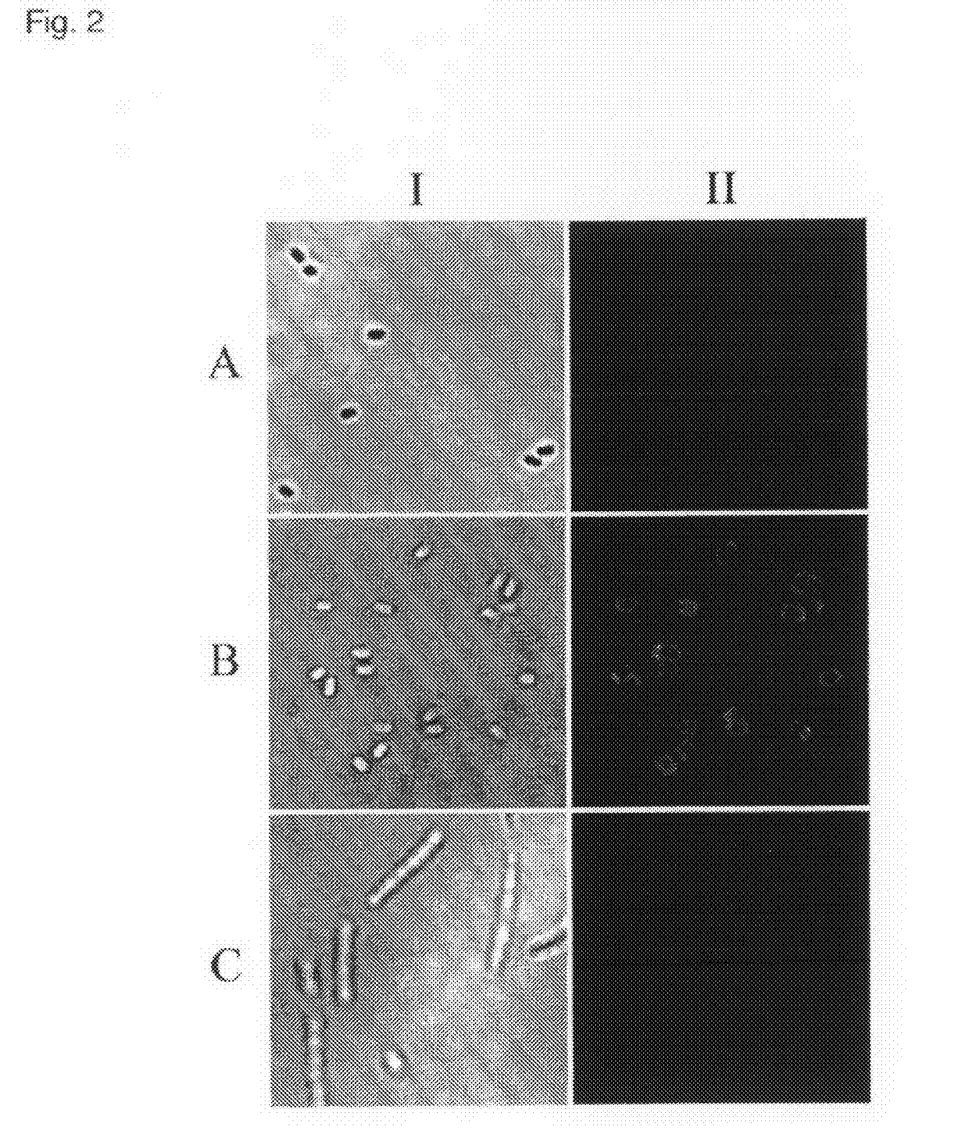
FIG. 2 shows indirect immunofluorescent staining of *B. anthracis* and *B. cereus* endospores by a monoclonal antibody (mAb) generated against the tetrasaccharide conjugate of formula 1b.
Figure 3:
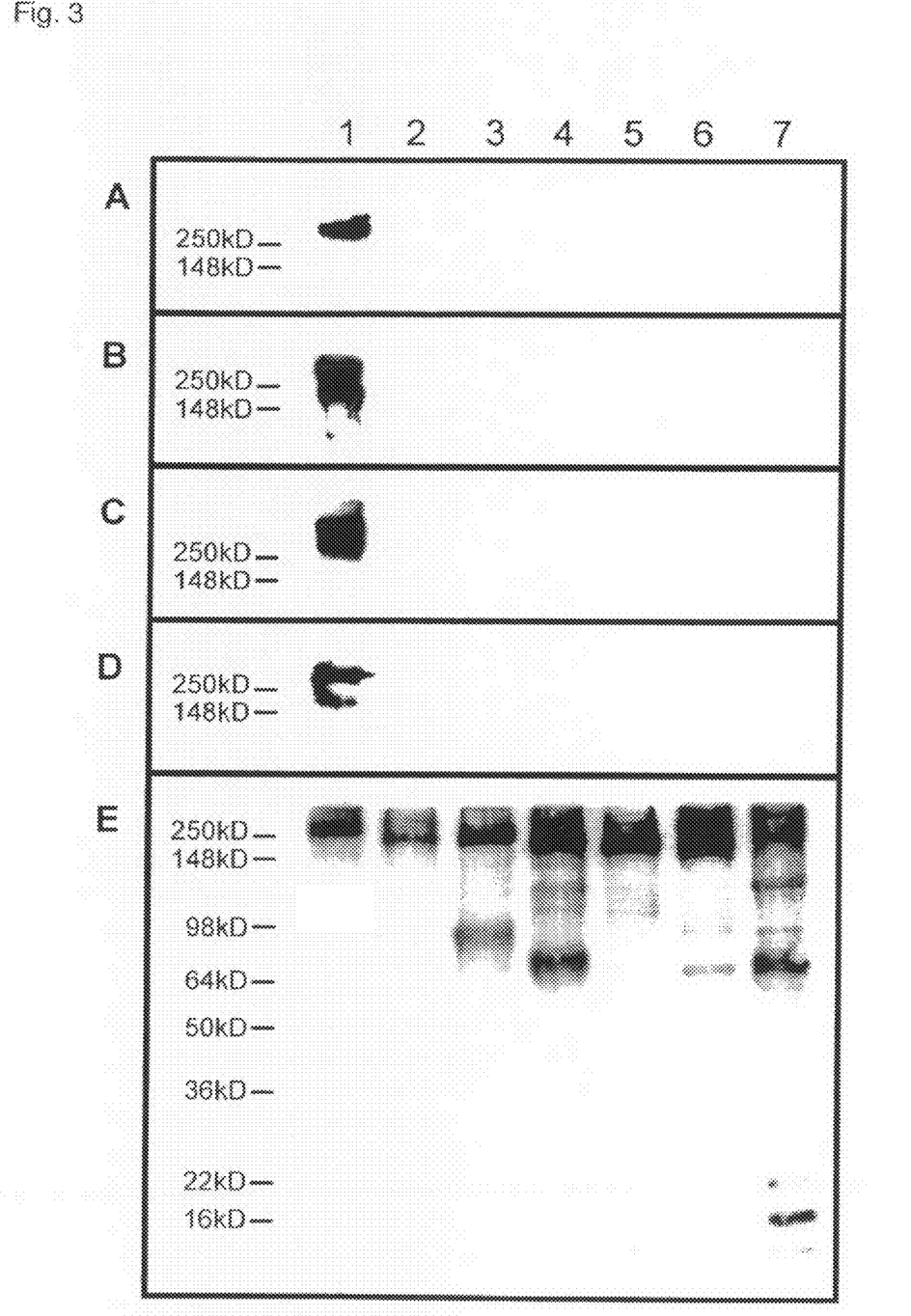
FIG. 3: Western blot analysis of the reactivity of anti-tetrasaccharide monoclonal antibody (mAb) MTA1 (A), anti-tetrasaccharide antisera (B), anti-disaccharide antisera (C), anti-anthrose antisera (D), and anti-*B. thuringiensis* antisera (E) with *Bacillus* species as the antigen. Total spore-lysates of *B. anthracis* (lane 1), *B. cereus* strains JF3652, JF3653, JF3654, JF3655, and JF3656 (lanes 2-6) and *B. thuringiensis* (lane 7) were separated by SDS—10% PAGE under reducing conditions and blotted onto a nitrocellulose membrane. All immunological reagents specific for the synthetic carbohydrates recognized a single band of about 250 kDa only in lanes containing lysates of *B. anthracis* endospores. In contrast, anti-*B. thuringiensis* immune sera exhibited cross-reactivity with all tested strains. All serum samples were used at a dilution of 1:1000 and the mAb at a concentration of 0.01 mg/ml.

The synthesis of a unique disaccharide 1 (R=H), corresponding trisaccharide 1a (R=H), tetrasaccharide 1b (R=H), and pentasaccharide 1c (R=H), found on the surface of the major glycoprotein BclA of *Bacillus anthracis* spores, its conjugation to a carrier protein and the generation of monoclonal anti-carbohydrate antibodies against these oligosaccharides are subject of this invention. The monoclonal anti-carbohydrate antibodies obtained by hybridoma formation are ideally suited for the highly selective detection of *B. anthracis* spores. Antibodies selective for the oligosaccharide of formula 1 are superior to pre-existing detection systems for *B. anthracis*. PCR-based assays or traditional phenotyping of bacteria are most accurate but complex, expensive and slow. State of the art antibody binding to spore surface peptide and protein antigens is less complicated although it is plagued by higher false-positive and false-negative readouts. The similarity of spore cell surface antigens of the opportunistic human pathogen *B. cereus* and other bacteria of this group such as *B. thuringiensis* and *B. mycoides* makes it difficult to create selective, reliable antibody-based detection systems. The specific, polyclonal and monoclonal antibodies produced against, for example, the synthetic tetrasaccharide antigen of formula 1b display the specificity that has been missing for peptide and protein antigens. The distinct differences in cell surface carbohydrate antigens provide the basis for the creation of selective antibody-based detection systems as demonstrated for *B. anthracis* by the present invention. Furthermore, the oligosaccharide conjugate with a carrier protein of formula 1 is useful as a vaccine against *B. anthracis* infection, either by active or by passive immunization methods.

In one aspect, the invention relates to conjugates of oligosaccharide of formula 1, wherein R is composed of zero to three saccharide units, a linker and a carrier protein, in particular to the conjugate of trisaccharide of formula 1a, wherein R is composed of zero, one or two saccharide units, a linker and a carrier protein, and more particularly to the conjugate of tetrasaccharide of formula 1b, wherein R is composed of zero or one saccharide units, a linker and a carrier protein, or to the conjugate of pentasaccharide of formula 1c, wherein R is composed of a linker and a carrier protein. The novel pentasaccharide of formula 1c, wherein R is hydrogen or a protecting group, is a further object of the invention. In compounds of formula 1c, the stereo center indicated with an asterix may be in the α form (shown in the formula) or in the corresponding anomeric β form.

Carrier proteins considered are proteins which by themselves do not display particular antigenic properties, but are supporting immunogenic reaction of a host to antigens (epitopes) displayed at the surface of the carrier protein. Suitable carrier proteins are, for example, bovine serum albumin (BSA), diphtheria toxoid, tetanus toxoid, heat shock proteins, viral coat proteins, heat labile enterotoxin or keyhole limpet hemocyanine (KLH).

Linkers are short bifunctional units, which themselves do not display antigenic properties, but which allow attaching the oligosaccharide unit of formula 1 to carrier proteins, resulting in a carrier protein displaying one or more, for example 1 to 100, in particular between 1 and 20, more particularly between 3 and 9, tetrasaccharide units exposed on its surface. Particular linkers considered are alkylene groups of 1 to 20 carbon atoms, in particular 3 to 10 carbon atoms, e.g. an alkylene group —$(CH_2)_4$—, such alkylene groups wherein the carbon atom connected to the carrier protein is a carbonyl group C=O, alkylene groups wherein one carbon atom is replaced by a nitrogen atom and the neighbouring carbon atom is a carbonyl group representing an amide function —C(=O)NH—, alkylene groups wherein one carbon atom is replaced by an oxygen atom and the neighbouring carbon atom is a carbonyl group representing an ester function —C(=O)O—, alkylene groups which are attached to the carrier protein through a mercaptosuccinimide, mercaptoacetyl or disulfide function, alkylene groups which are attached to the carrier protein through a 1,2,3-triazole ring, or polyether groups comprising 1 to 10 carbon atoms and 1 to 5 oxygen atoms, for example a polyethyleneoxide chain of the formula —$(CH_2CH_2O)_n$—, wherein n is between 1 and 5, and combinations of such polyethyleneoxide units with a carbonyl group C=O connecting the linker to the carrier protein.

Saccharides considered as components of R are, for example, the saccharides L-rhamnose, N-acetyl-D-galactosamine, or also D-galactose, D-mannose, D-glucosamine, or D-fucose. These saccharides are connected to the oligosaccharides of formula 1, 1a and 1b through a glycosidic bond in various different connectivities, usually in 1-3 connectivity. For example, N-acetyl-D-galactosamine is connected with L-rhamnose 1-3, and the stereo center indicated by an asterix may be in the α configuration as shown in formula 1c, but may also be in the corresponding β configuration.

Protecting groups are those customarily considered in sugar chemistry, for example those mentioned in "Protective Groups in Organic Synthesis", 3$^{rd}$ edition, T. W. Greene and P. G. M. Wuts (Ed.), John Wiley and Sons, New York, 1999.

The invention further relates to the manufacture of the conjugates of the invention. Such conjugates are obtained by synthesis of the oligosaccharide of formula 1, 1a, 1b, or 1c, (R=H) respectively, in suitably protected form, attaching a precursor of a linker to give a functionalized oligosaccharide, wherein R is a linker as defined hereinbefore or a linker precursor, and coupling one or more of these functionalized oligosaccharides to a carrier protein.

In a particular method of manufacture of a conjugate according to the invention, a compound of formula 1, 1a, 1b, or 1c, wherein R is an unsaturated alkyl group with 3 to 20 carbon atoms, is treated with ozone, and the obtainable intermediate aldehyde is conjugated to the carrier protein carrying amino functions under reducing conditions. Such reducing conditions are those customarily used in reductive amination, for example hydrogen gas in the presence of a suitable catalyst, or preferably sodium cyanoborohydride. Thereby the intermediate aldehyde forms imine functions with free amine groups of the carrier protein, which are reduced in situ into (saturated) amine functions.

Alternatively, a compound of formula 1, 1a, 1b, or 1c, wherein R is an unsaturated alkyl group with 3 to 20 carbon atoms, is treated with mercaptoacetic acid with radical generating catalysts or UV light. Treatment with a base generates an intermediate thiol which reacts with a pretreated carrier protein carrying maleimido functions to give an alkylmercaptosuccinimide linker. Alternatively, the reaction with a pretreated carrier protein carrying iodoacetyl functions gives an alkylmercaptoacetyl linker. Reaction with a correspondingly reduced carrier protein with free mercapto functions under oxidizing conditions creates alkylmercapto linkers bound to the carrier protein through disulfide bridges.

In a further method of manufacture, a compound of formula 1, 1a, 1b, or 1c, wherein R is an alkyl group of 1 to 10 carbon atoms with a terminal carboxyl function, is activated and coupled to the carrier protein using amide bond forming condensation conditions well known in amino acid and protein chemistry. This method is also suitable for the preparation of conjugates wherein the alkylene linker further comprises an amide or ester function as defined hereinbefore, or wherein the linker represents a polyethyleneoxide group.

In a further method of manufacture, a compound of formula 1, 1a, 1b, or 1c, wherein R is an alkyl group of 1 to 10 carbon atoms with a terminal amino function, may be reacted with a carrier protein wherein free carboxyl groups are activated, or may be attached to other appropriate electrophilic moieties on the surface of the carrier protein. Alternatively, in compounds of formula 1, 1a, 1b, or 1c, wherein R is an alkyl group of 1 to 10 carbon atoms with a terminal azido function, this may be reacted with properly functionalized carrier protein carrying alkyne functions in a reaction called "click chemistry". Likewise, in compounds of formula 1, 1a, 1b, or 1c, wherein R is an alkyl group of 1 to 10 carbon atoms with a terminal alkyne function, this may be reacted with properly functionalized carrier protein carrying azido groups.

The synthesis of tetrasaccharide of formula 1b and of a particular conjugate may, for example, be accomplished as follows: Synthesis of the terminal anthrose 8 (in suitably protected form) starts from commercially available D-fucose 3 (for formula and experimental details see below under Examples). Suitably protected rhamnose 13 is obtained by standard methods. The assembly of the tetrasaccharide via a [2+2] approach commences with the reaction of known rhamnose derivative 14 with rhamnose derivative 13 to give a suitably substituted disaccharide 16. The second disaccharide (18) is assembled by glycosylation of 12, an intermediate in the synthesis of building block 13, with the anthrose unit 8. Coupling of the two disaccharides 16 and 18 give the required tetrasaccharide as the pentenyl derivative 2 after removing all permanent protecting groups and transforming the azide moiety into an amine with sodium in liquid ammonia, and coupling with 3-hydroxy-3-methylbutyric acid.

The disaccharide of formula 1 may be prepared from the corresponding protected disaccharide 18. The trisaccharide of formula 1a is available from the protected disaccharide 18 and rhamnose derivative 15. For the synthesis of pentasaccharide 1c it is preferable to use a [3+2] approach connecting a trisaccharide composed of two L-rhamnose units and N-acetyl-D-galactosamine with the disaccharide 18.

The terminal double bond in the pentenyl function of tetrasaccharide 2 is transformed by ozonolysis into in aldehyde functional group which is coupled via reductive amination using sodium cyanoborohydride in PBS buffer to a carrier protein. Suitable carrier proteins are, for example, BSA or KLH.

If BSA is used as the carrier protein, three to eight oligosaccharide moieties are attached via lysine residues to one BSA molecule depending on the concentration of the carbohydrate. Using other carrier proteins, the number of oligosaccharide residues per molecule of carrier protein can also be adjusted by variation of the concentration of the oligosaccharide.

The invention further relates to antibodies specific for oligosaccharides of formula 1, in particular a polyclonal or monoclonal antibody against a conjugate as defined hereinbefore, and fragments thereof which retain the specificity to the oligosaccharides of formula 1. Preferred are monoclonal antibodies, for example IgG or IgM antibodies. Most preferred are monoclonal antibodies of mouse origin and such antibodies carrying human light and heavy chains, and humanized antibodies. Fragments of antibodies considered are Fab, Fab', F(ab')$_2$, scFv and Fv fragments.

To prepare antibodies according to the invention, conjugates of oligosaccharide of formula 1 with carrier proteins are used to immunize suitable animals. Animals considered for polyclonal antibody preparation are, for example mice, rats, chicken, guineas pigs, goats or horses, preferably mice or rats, in particular mice. For immunization the conjugates of the invention are optionally mixed with adjuvants, for example Freund's Adjuvant, ImmunEasy™ (QIAGEN, Inc.), Immune-stimulating complexes (ISCOMS), Alum, Ribi Adjuvant System (Ribi Immunochem Research, Inc.), Titer-Max (CytRx Corporation), Syntex Adjuvant Formulation (Chiron Corporation), SuperCarrier (Syntex Research), Montanide (ISA Seppic), Gerbu adjuvant (C-C Biotech) or other adjuvants known in the art. Animals are usually immunized subcutaneously and/or intraperitoneally, and conjugates according to the invention are injected at intervals of two to four weeks for one to five times.

Ascites or serum of immunized animals is isolated and polyclonal antibodies purified according to standard procedures. For example antibodies will be purified by affinity chromatography using solid supports covalently loaded with protein A, protein G or the targeted carbohydrate antigen.

Alternatively, immunized animals are sacrificed, spleens isolated, and spleen cell fused to suitable cells of cell lines generating B cell hybridoma. Suitable cell lines for immortalizing spleen cells are, for example, mouse myeloma cells, e.g. PAI or PAI-O cells.

Preferred mice for the production of monoclonal antibodies according to the invention are mice carrying human immunoglobulin Cγ1 heavy and Cκ light chain gene segments (G. Pluschke, A. Joss, J. Marfurt, C. Daubenberger, O. Kashala, M. Zwickl, A. Stief, G. Sansig, B. Schläpfer, S. Linkert, H. van der Putten, N. Hardman, M. Schroder, *J. Immunol. Meth.*, 1998, 215, 27-37). Alternatively, the "humanization" of monoclonal antibodies may be performed according to standard procedures at the stage of hybridoma cells through genetic engineering techniques, for example the combination of the gene segments encoding the mouse Ig heavy and light chain variable regions with gene segments encoding entire or partial gene segments encoding human Ig heavy and light chain constant regions, respectively. Alternatively the gene segments encoding the mouse Ig heavy and light chain complementarity determining regions (CDRs) are grafted onto human antibodies by combining them with gene segments encoding framework regions of human Ig variable region gene segments.

In a particular example, a conjugate of tetrasaccharide 1b with keyhole limpet hemocyanine (KLH) carrier protein formulated in ImmunEasy™ adjuvant (QIAGEN) elicited tetrasaccharide binding IgG antibodies following the second booster immunization in mice. B cell hybridoma lines producing tetrasaccharide specific monoclonal IgG antibodies (mAbs) are generated from spleen cells of one of the immunized mice. In an indirect immunofluorescence assay mAbs of three hybridoma cell lines bind specifically native *B. anthracis* endospores, but not to *B. cereus* and *B. subtilis* endospores.

The hybridoma cell line MTA1 was deposited for patent purposes at the "Deutsche Sammlung von Mikroorganismen und Zellkuluren GmbH (DSMZ)" on Jun. 15, 2006 and was allocated the number DSM ACC2792. The address of the depository is: DSMZ-Deutsche Sammlung von Mikroorganismen und Zellkulturen GmbH (DSMZ), Mascheroder Weg 1b, D-38124 Braunschweig, Germany.

The invention furthermore relates to kits comprising the antibodies of the invention. Kits as such are well known in the art and are adapted to a particular use. For example, if the antibodies of the invention are mouse antibodies, such a kit may contain a (second) anti-mouse antibody carrying a suitable marker, for example a fluorescent marker, which allows easy and rapid detection of the antibodies of the invention. Furthermore, the kit may contain standard equipment, solutions and directions for use to perform the diagnostic tests, conjugates of the invention and/or control peptides as standards, and the like.

The antibodies as described hereinbefore and the kits containing such antibodies may be used in an assay for the detection of *B. anthracis* spores. Such an assay is performed as known in the art. The antibodies of the invention are suitable for all direct and indirect antigen detection assays (such as ELISA, RIA, Western blotting, mass spectroscopy-coupled antigen capture systems) including sandwich assays with an antigen capture system coupled with an antibody-based detection system. Detecting antibodies are, for example, conjugates with a marker such as a dye (detected by its colour), fluorescence dye (detected by its fluorescence), enzyme (detected by its reaction leading e.g. to colour change or other visible result), radioisotope (detected by radioactivity measurement), or other particle creating a detectable result.

For example, probes to be tested whether they contain endospores of *B. anthracis* are added to microscope glass slides, air-dried and fixed. Slides are then incubated with antibodies of the invention, for example monoclonal mouse antibodies. After extensive washing, the slides are developed with a second antibody reacting with the antibody of the invention, e.g. a goat anti-mouse antibody, further carrying a fluorescent dye. Antibody binding is then assessed by fluorescence microscopy.

The invention furthermore relates to a vaccine for the prevention of *B. anthracis* infection comprising a conjugate of the invention as defined hereinbefore and an adjuvant. Such vaccines may be used to treat animals including humans to prevent infection by *B. anthracis*. The oligosaccharide antigen may be coupled to the carrier proteins mentioned above or to other suitable particles, and will be administered repeatedly in combination with an adjuvant by a suitable route (such as intramuscularly, subcutaneously, orally or the like) prior to exposure or after exposure to the pathogen suspected to be *B. anthracis*. Suitable adjuvants may be one of those mentioned above in the immunization of animals, preferably those used in human vaccination.

Treatment of *B. anthracis* infections with antibodies of the invention by so-called passive antibody therapy is also considered. Preferred antibodies for this purpose are humanized antibodies, which reduce side effects of the treatment such as anaphylactic reaction.

EXAMPLES

General Methods

All chemicals used were reagent grade and used as supplied except where noted. Dichloromethane ($CH_2Cl_2$) was purchased from JT Baker and purified by a Cycle-Tainer Solvent Delivery System. Pyridine and acetonitrile were refluxed over calcium hydride and distilled prior to use. Analytical thin-layer chromatography was performed on E Merck silica gel 60 $F_{254}$ plates (0.25 mm). Compounds were visualized by dipping the plates in a cerium sulfate ammonium molybdate solution or a sulfuric acid/methanol solution followed by heating. Liquid chromatography was performed using forced flow of the indicated solvent on Sigma H-type silica (1040 mm). $^1$H NMR spectra were obtained on a Varian VXR-300 (300 MHz), Bruker-600 (600 MHz) and are reported in parts per million (δ) relative to $CHCl_3$ (7.26 ppm) or in the case of $CD_3OD$ as solvent relative to TMS (0.00 ppm). Coupling constants (J) are reported in Hertz. $^{13}$C NMR spectra were obtained on a Varian VXR-300 (75 MHz), Bruker-600 (150 MHz) and are reported in δ relative to $CDCl_3$ (77.0 ppm) as an internal reference or to TMS (0.00 ppm).

Synthesis of Tetrasaccharide 2 and Conjugation to a Carrier Protein

Synthesis of the terminal anthrose started from commercially available D-fucose (3). Acetylation of 3, followed by immediate protection of the anomeric center with p-methoxyphenol (MPOH) and subsequent cleavage of the acetates furnished 4. A levulinoyl group proved to be the best choice to protect the C2 hydroxyl during installation of the β(1→3) glycosidic linkage in anticipation of its selective removal prior to O-2 methylation. Thus, reaction of 4 with 2,2-dimethoxypropane and introduction of the C2-O-levulinic ester furnished 5. Removal of the isopropylidene and tin-mediated, selective benzylation of the C3 hydroxyl group afforded 6. Inversion of the stereochemistry at C4 was achieved by reaction of the hydroxyl group with triflic anhydride to install a triflate that is displaced by sodium azide in an $S_N$2-type fashion to give 7 (J. Golik, H. Wong, B. Krishnan, D. M. Vyas, T. W. Doyle, *Tetrahedron Lett.* 1991, 32, 1851-1854). Removal of the anomeric p-methoxyphenyl group using wet cerium ammonium nitrate was followed by the formation of the anthrose trichloroacetimidate 8 using trichloroacetonitrile and a catalytic amount of sodium hydride.

3

4

6

8

9

10

11

12

13

Reagents and conditions: a) Ac$_2$O, pyridine, 12 h, quant.; b) MPOH, BF$_3$.OEt$_2$, acetone, 0° C.→25° C., 12 h, 71%; c) NaOMe, MeOH, 6 h, quant.; d) 2,2-dimethoxypropane, BF$_3$OEt$_2$, acetone, 0° C.→25° C., 12 h, 96%; e) LevOH, DMAP, DIPC, CH$_2$Cl$_2$, 0° C., 3 h, 92%; f) HCl (pH 3), MeOH, 50° C., 18 h, 85%; g) n-Bu$_2$SnO, toluene, Dean-Stark, reflux, 2 h; h) BnBr, TBAI, toluene, reflux, 3 h, 95% (2 steps); i) Tf$_2$O, pyridine, 0° C., 90 min; j) NaN$_3$, DMF, 25° C., 10 h, 80% (2 steps); k) CAN, H$_2$O/CH$_3$CN, 25° C., 1 h; l) Cl$_3$CCN, NaH, CH$_2$Cl$_2$, 25° C., 45 min, 78% (2 steps). MPOH=p-methoxyphenol, LevOH=levulinic acid, DMAP=4-dimethylaminopyridine, DIPC=diisopropyl carbodiimide, TBAI=tetrabutylammonium iodide, CAN=cerium ammonium nitrate.

Rhamnose building block 13, equipped with a robust C2 participating group to ensure α selectivity and a readily removable temporary protecting group in position 3 was synthesized next. Placement of an anomeric p-methoxyphenol gave 10 (K. Sarkar, I. Mukherjee, N. Roy, *J. Carbohydr. Chem.* 2003, 22, 95-107). Formation of the cis-fused acetal and subsequent benzylation afforded 11. The transformation of the acetal to the corresponding orthoester and ring-opening resulted in the kinetically preferred axial acetate in 12. Placement of Fmoc, cleavage of the p-methoxyphenyl glycoside and reaction with trichloroacetonitrile in the presence of traces of sodium hydride afforded building block 13.

Reagents and conditions: a) Ac$_2$O, pyridine, 12 h, quant.; b) MPOH, BF$_3$—OEt$_2$, acetone, 0° C.→25° C., 12 h, 80%; c) NaOMe, MeOH, 12 h, 96%; d) 2,2-dimethoxypropane, BF$_3$—OEt$_2$, acetone, 0° C.→25° C., 12 h, 84%; e) NaH, BnBr, DMF, 0° C.→25° C., 4 h, quant.; f) HCl (pH 3), MeOH, 50° C., 89%; g) 1,1,1-triethoxyethane, p-TsOH (cat.), DMF, 50° C., 50 min; h) AcOH/H$_2$O (4/1, v/v), 10° C., 10 min, 98% (2 steps); i) FmocCl, pyridine, 25° C., 2 h, 88%; j) CAN, H$_2$O/CH$_3$CN, 25° C., 1 h, 76%; k) Cl$_3$CCN, NaH, CH$_2$Cl$_2$, 25° C., 1 h, 94%. MPOH=p-methoxyphenol, Fmoc=fluorenylmethoxycarbonyl, CAN=cerium ammonium nitrate.

The assembly of the tetrasaccharide via a [2+2] approach commenced with the reaction of known building block 14 (A. Fürstner, T. Müller, *J. Am. Chem. Soc.* 1999, 121, 7814-7821) with 4-penten-1-ol. The pentenyl moiety serves at a later stage as a handle for conjugation to a carrier protein in the preparation of the vaccine candidate. Removal of acetate, further glycosylation with 13 and subsequent removal of Fmoc yielded disaccharide 16. During the cleavage of Fmoc minor acetate migration (~10%) from the C2 to C3 hydroxyl was observed, but the undesired product was easily removed by column chromatography.

The second disaccharide was assembled by glycosylation of 12, an intermediate in the synthesis of building block 13, with the anthrose unit 8. The levulinoyl group that ensured β-selectivity was replaced by the final C2 methoxy substituent. The methylation was achieved with MeI/Ag$_2$O in the presence of catalytic amount of dimethyl sulfide. The commonly used maneuver to convert the methoxyphenyl glycoside into the corresponding trichloroacetimidate furnished disaccharide unit 18.

c) 13, TMSOTf, CH$_2$Cl$_2$, 0° C., 1 h, 91%; d) piperidine, DMF, 25° C., 30 min, 89%; e) 8, TMSOTf, CH$_2$Cl$_2$, 0° C., 1 h, 90%; f) hydrazinium acetate, CH$_2$Cl$_2$, MeOH, 25° C., 12 h, quant.; g) MeI, Ag$_2$O, THF, Me$_2$S (cat.), 25° C., 8 h, 73%; h) CAN, H$_2$O/CH$_3$CN, 25° C., 1 h; i) Cl$_3$CCN, NaH, CH$_2$Cl$_2$, 25° C., 1 h 95% (2 steps). TMSOTf=trimethylsilyl triflate, MPOH=p-methoxyphenol, CAN=cerium ammonium nitrate.

To complete the total synthesis, the two disaccharide units 16 and 18 were unified to afford tetrasaccharide 19. Sodium in liquid ammonia removed all permanent protecting groups and transformed the azide moiety into an amine, thus achieving global deprotection. The formation of the amide with 3-hydroxy-3-methylbutyric acid under peptide coupling conditions (L. A. Carpino, A. El-Faham, *J. Org. Chem.* 1995, 60, 3561-3564) led to tetrasaccharide 2.

Reagents and conditions: a) 4-pentenol, TMSOTf, CH$_2$Cl$_2$, −20° C., 45 min, 79%; b) NaOMe, MeOH, 4 h, 96%;

Reagents and conditions: a) TMSOTf, CH$_2$Cl$_2$, 0° C., 70 min, 73%; b) Na/NH$_3$(l), THF, −78° C., 60%; c) 3-hydroxy-3-methylbutyric acid, HATU, DIPEA, DMF, 25° C., 2 h, 75%. TMSOTf=trimethylsilyl triflate, HATU=N-[(dimethylamino)-1H-1,2,3-triazolo[4,5-b]pyridin-1-ylmethylene]-N-methylmethan-aminium hexafluorophosphate, DIPEA=diisopropylethyl amine.

The terminal double bond of tetrasaccharide 2 was transformed by ozonolysis into in aldehyde moiety which was coupled via reductive amination using sodium cyanoborohydride in PBS buffer to a carrier protein such as BSA or KLH. Depending on the concentration of the carbohydrate three to eight tetrasaccharide moieties were attached via lysine residues to one BSA molecule.

4-Methoxyphenyl α-D-fucopyranoside (4). D-Fucose (3) (4.95 g, 30.14 mmol) was dissolved in 30 mL of acetic anhydride and 30 mL of pyridine and stirred for 12 h. The solvent was removed in vacuo. Column chromatography (2:1 hexane/EtOAc) yielded 10.15 g (quant.) of 1,2,3,4-tetraacetyl-D-fucose (as a mixture of α-and β-anomer). 1,2,3,4-tetraacetyl-D-fucose (20.0 g, 60.2 mmol) and p-methoxyphenol (MPOH) (10.46 g, 84.3 mmol) were dissolved in 220 mL of dichloromethane and cooled to 0° C. $BF_3.OEt_2$ (21.4 g, 19.0 mL, 150.5 mmol) was added and the mixture stirred overnight. The reaction mixture was quenched by addition of saturated $NaHCO_3$ solution, washed 2 times with water, dried over $Na_2SO_4$, concentrated and the residue was purified by column chromatography (3:1 hexane/EtOAc) yielding 16.8 g (71%) of 4-methoxyphenyl 1,2,3,4tetraacetyl-α-D-fucose (Only the β-anomer reacts, α-anomer could be recovered). 4-methoxyphenyl 1,2,3,4-tetraacetyl-α-D-fucose (3.90 g, 9.85 mmol) was dissolved in 150 mL of methanol and 6 mL of 0.5 M NaOMe solution were added. The mixture was stirred for 6 h. The solvent was removed in vacuo. Column chromatography (3:1 dichloromethane/methanol) afforded 2.63 g (99%) as a colorless solid: $[\alpha]_D$: +201.6 (c=0.32, $CH_3OH$). $^1H$ NMR ($CD_3OD$, 300 MHz) δ 1.18 (d, J=6.6 Hz, 3H), 3.74 (s, 3H), 3.89 (m, 2H), 4.09 (quart., J=6.0 Hz, 1H), 5.31 (d, J=3.6 Hz, 1H), 6.82 (d, J=9.3 Hz, 2H), 7.04 (d, J=9.3 Hz, 2H). $^{13}C$ NMR ($CD_3OD$, 75 MHz) δ16.3, 55.7, 67.9, 69.5, 71.2, 73.2, 100.0, 115.1, 119.0, 152.2, 156.0. MALDI-HRMS: m/z $[M+Na]^+$ calcd 293.0996, obsd 293.0994.

4-Methoxyphenyl 3,4-O isopropylidene-2-O-levulinoyl-α-D-fucopyranoside (5). 4-Methoxyphenyl α-D-fucopyranoside (4) (500 mg, 1.85 mmol) was suspended in 15 mL of acetone. 2,2-dimethoxypropane (327 mg, 0.385 mL, 3.15 mmol) was added in one portion and the mixture cooled to 0° C., then $BF_3.OEt_2$ (40 mg, 0.28 mmol) was added dropwise. The mixture was stirred for 12 h. Afterwards the reaction was quenched by addition of 0.2 ml of pyridine. The volatiles were removed in vacuo. The resulting crude product was purified by flash chromatography (3:1 hexane/EtOAc) to afford 551 mg (96%) of 4-Methoxyphenyl 3,4-isopropylidene-D-fucopyranoside as a colorless oil. 4-Methoxyphenyl 3,4-O isopropylidene-α-D-fucopyranoside (3.30 g, 10.65 mmol), levulinic acid (1.36 g, 1.20 mL, 11.71 mmol), DMAP (1.43 g, 11.71 mmol) and diisopropyl carbodiimide (1.34 g, 1.65 mL, 10.65 mmol) are dissolved at 0° C. in 35 mL of dichloromethane and stirred for 3 h. The reaction mixture is diluted with 80 ml of hexane/EtOAc (3:1) and flushed through a 3 cm plug of silica gel. The filtrate was concentrated and purified by column chromatography (3:1→2:1 hexane/EtOAc) yielding 4.01 g (92%) of 5 as a colorless oil: $[\alpha]_D$: +162.4 (c=0.95, $CHCl_3$). IR (thin film, $CHCl_3$): 3008, 1740, 1719, 1506, 1384, 1158, 1078 $cm^{-1}$. $^1H$ NMR ($CDCl_3$, 300 MHz) δ 1.31-1.38 (m, 6H), 1.55 (s, 3H), 2.15 (s, 3H), 2.65-2.78 (m, 4H), 3.77 (s, 3H), 4.15 (dd, J=5.4 Hz, J=2.4 Hz, 1H), 4.27 (m, 1H), 4.49 (dd, J=8.1 Hz J=5.1 Hz, 1H), 5.01 (dd, J=8.1 Hz, J=3.9 Hz, 1H), 5.44 (d, J=3.9 Hz 1H), 6.83 (d, J=9.0 Hz, 2H), 6.98 (d, J=9.0 Hz, 2H). $^{13}C$ NMR ($CDCl_3$, 75 MHz) δ13.4, 26.5, 28.0, 28.1, 29.8, 37.9, 55.6, 63.9, 71.8, 73.3, 76.0, 95.6, 109.4, 114.5, 117.7, 150.5, 154.9, 172.1, 205.9. MALDI-HRMS: m/z $[M+Na]^+$ calcd 431.1676, obsd 431.1683.

4-Methoxyphenyl 3-O-benzyl-2-O-levulinoyl-α-D-fucopyranoside (6). 4-Methoxyphenyl 3,4-O-isopropylidene-2-O-levulinoyl-α-D-fucopyranoside (5) (449 mg, 1.10 mmol) was dissolved in 5 mL of methanol and 0.5 mL of water. An aqueous solution of 3.7% hydrochloric acid was added (some drops) until pH 3 was reached. The mixture was heated to 50° C. and stirred for 18 h until the TLC showed complete conversion. The mixture was extracted with EtOAc, washed 2 times with $NaHCO_3$, dried over $Na_2SO_4$ and was concentrated. The resulting crude product was purified by flash chromatography (2:1→1:1→1:2 hexane/EtOAc) to afford 345 mg (85%) of 4-Methoxyphenyl 2-0 levulinoyl-α-D-fucopyranoside as a colorless oil.

4-Methoxyphenyl 2-O-levulinoyl-α-D-fucopyranoside (2.37 g, 6.46 mmol) and dibutyl tin oxide (1.61 g, 6.46 mmol) are dissolved in 70 mL of toluene. The mixture was refluxed with a Dean-Stark trap for 2.5 h. Then it was cooled to 60° C., benzylbromide and tetrabutylammonium iodide were added and refluxed for 2 h. After cooling to room temperature the reaction mixture was diluted with water and extracted 3 times with EtOAc, dried over $Na_2SO_4$ and concentrated. The crude product was purified by column chromatography (3:2 hexane/EtOAc) yielding 2.82 g (95%, 2 steps) of 6 as a colorless oil: $[\alpha]_D$: +140.8 (c=0.35, $CHCl_3$). IR (thin film, $CHCl_3$): 3015, 1739, 1713, 1503, 1362, 1050 $cm^{-1}$. $^1H$ NMR ($CDCl_3$, 300 MHz) δ 1.29 (d, J=6.6 Hz, 3H), 2.14 (s, 3H), 2.62 (m, 3H), 2.72 (m, 2H), 3.76 (s, 3H), 3.92 (s, 1H), 4.09 (m, 2H), 4.74 (s, 2H), 5.28 (dd, J=10.2 Hz J=3.9 Hz, 1H), 5.50 (m, 1H), 6.82 (d, J=9.0 Hz, 2H), 6.98 (d, J=9.0 Hz, 2H), 7.33 (m, 5H). $^{13}C$ NMR ($CDCl_3$, 75 MHz) δ16.2, 28.1, 29.9, 37.9, 55.7, 66.2, 69.8, 70.0, 72.4, 75.6, 96.2, 114.5, 118.0, 118.2, 127.6, 127.7, 127.9, 128.5, 137.7, 150.7, 155.0, 172.0, 206.0. MALDI-HRMS: m/z $[M+Na]^+$ calcd 481.1833, obsd 481.1824.

4-Methoxyphenyl 4-azido-3-O-benzyl-6-desoxy-2-O-levulinoyl-α-D-glucopyranoside (7). 4-Methoxyphenyl 3-O-benzyl-2-O-levulinoyl-α-D-fucopyranoside (6) (971 mg, 2.12 mmol) was azeotroped 2 times with toluene and dissolved in 20 mL of dichloromethane. Pyridine (1.84 g, 1.87 mL, 23.3 mmol) was added and the mixture cooled to 0° C. Triflic anhydride (1.19 g, 0.71 mL, 4.24 mmol) was added and the mixture stirred for 90 min at 0° C. The mixture was quenched by addition of diluted $NaHCO_3$ solution, the phases were separated and the organic layer extracted 3 times with 3% hydrochloric acid, once with water, dried over $Na_2SO_4$ and was concentrated. The resulting crude product was azeotroped 3 times with toluene to remove all traces of pyridine and dried for 1 h in vacuo. The yellow product was dissolved in 25 mL of DMF and sodium azide (3.58 g, 55.1 mmol) was added, and the reaction mixture stirred overnight. The mixture was diluted with water and EtOAc, the phases were separated. The organic phase was washed 3 times with brine, dried over $Na_2SO_4$ and concentrated. Column chromatography (3:1 hexane/EtOAc) afforded 816 mg (80%, 2 steps) of 7 as a slightly yellow oil: $[\alpha]_D$: +192.6 (c=1.25, $CHCl_3$). IR (thin film, $CHCl_3$): 3015, 2103, 1739, 1713, 1503, 1400, 1359, 1159, 1034 $cm^{-1}$. $^1H$ NMR ($CDCl_3$, 300 MHz) δ 1.31 (d, J=6.3 Hz, 3H), 2.14 (s, 3H), 2.58 (m, 2H), 2.69 (m, 2H), 3.26 (t, J=9.9 Hz, 1H), 3.77 (s, 3H), 3.83 (m, 1H), 4.08 (m, 1H), 4.84 (d, J=10.8 Hz, 1H), 4.90 (d, J=10.8 Hz, 1H), 4.96 (dd, J=9.9 Hz, J=3.6 Hz, 1H), 5.48 (d, J=3.3 Hz, 1H), 6.83 (d, J=9.0 Hz, 2H), 6.99 (d, J=9.0 Hz, 2H), 7.31-7.42 (m, 5H). $^{13}C$ NMR ($CDCl_3$, 75 MHz). δ18.4, 28.0, 29.8, 37.8, 55.7, 66.8, 67.9, 73.6, 75.4, 76.6, 78.1, 95.7, 114.6, 118.2, 127.8, 127.8, 128.3, 137.8, 150.4, 155.2, 171.9, 205.7. MALDI-HRMS: m/z $[M+Na]^+$ calcd 506.1898, obsd 506.1889.

4-Azido-3-O-benzyl-6-desoxy-2-O-levulinoyl-α-D-glucopyranosyl trichloroacetimidate (8). 4-Methoxyphenyl 4-azido-3-O-benzyl-6-desoxy-2-O-levulinoyl-α-D-glucopyranoside (7) (2.02 g, 4.18 mmol) was dissolved in a mixture of 50 mL of acetonitrile and 50 mL of water. Cerium ammonium nitrate (6.87 g, 12.55 mmol) was added and the mixture stirred for 2 h at room temperature. After TLC showed complete removal of the MP group, the mixture was diluted with EtOAc, washed 2 times with brine, then with water, dried over $Na_2SO_4$ and was concentrated. The resulting crude product was purified by column chromatography (1:1→1:2 hexane/EtOAc) to afford 1.47 g (93%) of 4-azido-3-O-benzyl-6-desoxy-2-O-levulinoyl-α-D-glucopyranoside as a slightly yellow solid. This compound (300 mg, 0.796 mmol) was dissolved in 5 mL of trichloroacetonitrile and 4 mL of dichloromethane. A catalytic amount of sodium hydride (5 mg) was added, the solution turned brownish and was stirred for 45 min. TLC indicated complete conversion. The solvent was removed and the residue purified by flash column chromatography (3:1 hexane/EtOAc) to afford 322 mg (78%, 2 steps) of 8 (α/β 4:3) as a yellow oil: IR (thin film, $CHCl_3$): 2924, 2112, 1747, 1720, 1674, 1455, 1360, 1290, 1156 $cm^{-1}$. $^1H$ NMR ($CDCl_3$, 300 MHz) δ 1.34 (d, J=6.3 Hz, 3H, α), 1.40

(d, J=6.0 Hz, 3H, β), 2.15 (s, 3H), 2.46 (m, 2H), 2.68 (m, 2H), 3.29 (quart, J=9.6 Hz, 1H), 3.46 (m, 1H, β), 3.63 (t, J=9.3 Hz, 1H, β), 3.81 (m, 1H, α), 3.96 (t, J=9.6 Hz, 1H, α), 4.71-4.87 (m, 2H), 5.03 (dd, J=9.9 Hz, J=3.6 Hz, 1H, α), 5.26 (t, J=9.0 Hz, 1H, β), 5.71 (d, J=8.1 Hz, 1H, β), 6.40 (d, J=3.3 Hz, 1H, α), 7.26-7.37 (m, 5H), 8.60 (s, 1H, α), 8.64 (s, 1H, β). $^{13}$C NMR (CDCl$_3$, 75 MHz, α/β mixture). δ18.6, 18.6, 27.8, 27.9, 30.0, 37.8, 37.9, 67.5, 69.4, 72.1, 72.6, 72.9, 75.1, 75.5, 77.6, 81.2, 93.7, 95.8, 128.2, 128.4, 128.7, 137.6, 137.7, 161.0, 161.4, 171.2, 172.1, 206.1. MALDI-HRMS: m/z [M+Na]$^+$ calcd 543.0575, obsd 543.0567.

4-Methoxyphenyl α-L-rhamnopyranoside (10). L-Rhamnose (as monohydrate) (9) (25.0 g, 137.2 mmol) was dissolved in acetic anhydride (154 g, 1.51 mol) and pyridine (160 mL) and stirred for 12 h. The solvent was removed in vacuo. Column chromatography (2:1 hexane/EtOAc) yielded 45.3 g (quant.) of 1,2,3,4-tetraacetyl-L-rhamnose.

1,2,3,4-Tetraacetyl-L-rhamnose (19.2 g, 57.8 mmol) and p-methoxyphenol (MPOH) (12.2 g, 98.3 mmol) were dissolved in 150 mL of dichloromethane and cooled to 0° C. BF$_3$OEt$_2$ (23.0 g, 20.5 mL, 162.0 mmol) was added and the mixture stirred overnight while warming to room temperature. The reaction mixture was quenched by addition of saturated NaHCO$_3$ solution, washed 2 times with water, dried over Na$_2$SO$_4$, concentrated and the residue was purified by column chromatography (3:1 hexane/EtOAc) yielding 18.3 g (80%) of 4-methoxyphenyl 1,2,3,4-tetraacetyl-α-L-rhamnose. 4-Methoxyphenyl 1,2,3,4-tetraacetyl-α-L-rhamnose (18.0 g, 45.4 mmol) was dissolved in 300 mL of methanol and 9 mL of 0.5 M NaOMe solution were added. The mixture was stirred for 12 h, the solvent was removed in vacuo. Column chromatography (4:1 dichloromethane/methanol) afforded 2.63 g (96%) as a colorless solid.

4-Methoxyphenyl 4-O-benzyl-2,3-O-isopropylidene-α-L-rhamnopyranoside (11). 4-Methoxyphenyl α-L-rhamnopyranoside (9) (11.7 g, 43.3 mmol) was dissolved in 120 mL of acetone. 2,2-Dimethoxypropane (7.7 g, 9.1 mL, 73.7 mmol) was added in one portion and the mixture cooled to 0° C., then BF$_3$.OEt$_2$ (916 mg, 818 μL, 6.50 mmol) was added dropwise. The mixture was stirred for 12 h while warming to room temperature. Afterwards the reaction was quenched by addition of 1.0 mL of pyridine. The volatiles were removed in vacuo. The resulting crude product was purified by flash chromatography (3:1 hexane/EtOAc) to afford 11.25 g (84%) of 4-methoxyphenyl 2,3-isopropylidene-α-L-rhamnopyranoside as a colorless oil.

4-Methoxyphenyl 2,3-isopropylidene-α-L-rhamnopyranoside (7.50 g, 24.2 mmol) was dissolved in 75 mL of DMF and cooled to 0° C. Benzylbromide (8.28 g, 48.4 mmol) and sodium hydride (60% in oil) (1.94 g, 48.4 mmol) were added carefully. The mixture was stirred for 12 h while warming to room temperature. The solution was quenched with water and diluted with EtOAc. The phases were separated and the organic layer was washed 3 times with water, dried over Na$_2$SO$_4$ and concentrated. The crude product was purified by column chromatography (4:1 hexane/EtOAc) yielding 10.03 g (quant.) of 11 as a colorless oil: [α]$_D$: −91.4 (c=1.07, CHCl$_3$). IR (thin film, CHCl$_3$): 3007, 2937, 1507, 1454, 1388 cm$^{-1}$. $^1$H NMR (CDCl$_3$, 300 MHz) δ 1.25 (d, J=6.3 Hz, 3H), 1.44 (s, 3H), 1.56 (s, 3H), 3.30 (m, 1H), 3.77 (s, 1H), 3.87 (m, 1H), 4.37 (d, J=5.1 Hz, 1H), 4.44 (t, J=6.0 Hz, 1H), 4.67 (d, J=11.4 Hz, 2H), 4.94 (d, J=11.4 Hz, 2H), 5.62 (s, 1H), 6.84 (d, J=9.0 Hz, 2H), 6.99 (d, J=9.0 Hz, 2H), 7.28-7.40 (m, 5H). $^{13}$C NMR (CDCl$_3$, 75 MHz) δ17.8, 26.3, 27.9, 55.5, 65.3, 72.9, 75.9, 78.5, 80.9, 96.0, 109.4, 114.5, 117.6, 127.6, 127.9, 128.2, 138.2, 150.1, 154.8. MALDI-HRMS: m/z [M+Na]$^+$ calcd 423.1785, obsd 423.1777.

4-Methoxyphenyl 2-O-acetyl-4-O-benzyl-α-L-rhamnopyranoside (12). 4-Methoxyphenyl 2, 3-0 isopropylidene-4-O-benzyl-α-L-rhamnopyranoside (11) (9.38 g, 23.45 mmol) was dissolved in 100 mL of methanol and 10 mL of water. An aqueous solution of 3.7% hydrochloric acid was added until pH 3 was reached. The mixture was heated to 45° C. and stirred for 2 d until the TLC showed complete conversion. The mixture was extracted with EtOAc, washed 2 times with NaHCO$_3$, dried over Na$_2$SO$_4$ and was concentrated. The resulting crude product was purified by flash chromatography (2:1→1:1 hexane/EtOAc) to afford 7.52 g (89%) of 4-methoxyphenyl 4-O-benzyl-α-L-rhamnopyranoside as a colorless powder.

4-Methoxyphenyl 4-O-benzyl-α-L-rhamnopyranoside (4.06 g, 11.28 mmol) and 1,1,1-triethoxyethane (2.20 g, 2.47 mL, 13.53 mmol) are dissolved in 75 mL of DMF and stirred for 50 min at 50° C. DMF was removed in vacuo. The residue was dissolved in AcOH/H$_2$O (4:1, v/v) and stirred for 10 min at room temperature. The acetic acid is removed in vacuo and the crude product was purified by column chromatography (3:1 hexane/EtOAc) yielding 4.51 g (98%, 2 steps) of 12 as a colorless oil: [α]$_D$: −69.4 (c=1.25, CHCl$_3$). IR (thin film, CHCl$_3$): 3005, 2933, 1739, 1503, 1374, 1126, 1041 cm$^{-1}$. $^1$H NMR (CDCl$_3$, 300 MHz) δ 1.34 (d, J=6.0 Hz, 3H), 2.19 (s, 3H), 2.41 (b, 1H), 3.44 (t, J=9.3 Hz, 1H), 3.76 (s, 3H), 3.92 (m, 1H), 4.31 (d, J=9.0 Hz, 2H), 4.74 (d, J=12.6 Hz, 2H), 4.87 (d, J=12.6 Hz, 2H), 5.29 (m, 1H), 5.36 (s, 1H), 6.82 (d, J=9.0 Hz, 2H), 6.96 (d, J=9.0 Hz, 2H), 7.33 (m, 5H). $^{13}$C NMR (CDCl$_3$, 75 MHz) δ18.1, 21.2, 55.7, 68.1, 70.0, 72.6, 75.3, 81.6, 96.3, 114.5, 117.6, 127.8, 127.8, 128.4, 138.0, 149.9, 154.9, 170.6. MALDI-HRMS: m/z [M+Na]$^+$ calcd 425.1571, obsd 425.1565.

2-O-Acetyl-4-O-benzyl-3-O-fluorenylmethoxycarbonyl-α-L-rhamnopyranosyl trichloroacetimidate (13). 4-Methoxyphenyl 2-O-acetyl-4-O-benzyl-α-L-rhamnopyranoside (12) (4.57 g, 11.36 mmol) was dissolved in 60 mL of pyridine. FmocCl (5.88 g, 22.73 mmol) was added in one portion and the mixture stirred for 2 h at room temperature. Pyridine was removed in vacuo and the residue adsorbed on silica gel. 6.21 g (88%) of pure 4-methoxyphenyl 2-O-acetyl-4-O-benzyl-3-O-fluorenylmethoxycarbonyl-α-L-rhamnopyranoside were obtained by column chromatography (5:1→4:1→3:1 hexane/EtOAc). 4-Methoxyphenyl 2-O-acetyl-4-O-benzyl-3-O-fluorenylmethoxycarbonyl-α-L-rhamnopyranoside (3.10 g, 4.96 mmol) was dissolved in a mixture of 55 mL of toluene, 80 mL of acetonitrile and 55 mL of water. Cerium ammonium nitrate (21.7 g, 39.7 mmol) was added and the mixture was vigorously stirred for 80 min at room temperature. After TLC showed complete removal of the MP group, the phases of the mixture were separated, the organic phase was washed 2 times with water, saturated aqueous NaHCO$_3$, then again once with water, dried over Na$_2$SO$_4$ and was concentrated. The resulting crude product was adsorbed on silica gel and purified by column chromatography (3:1→2:1 hexane/EtOAc) to afford 1.95 g (76%) of 2-acetyl-4-benzyl-3-fluorenylmethoxycarbonyl-L-rhamnopyranoside as a slightly yellow solid. This compound (675 mg, 1.30 mmol) was dissolved in 6 mL of tricloroacetonitrile and 7 mL of dichloromethane. A catalytic amount of sodium hydride (10 mg) was added and the mixture stirred for 60 min. The solvent was removed in vacuo and the residue purified by flash column chromatography (2:1 hexane/EtOAc) to afford 810 mg (94%) of 13 (only traces of P product) as a slightly yellow oil: [α]$_D$: −17.3 (c=0.51, CHCl$_3$), IR (thin film, CHCl$_3$): 3026, 1754, 1672, 1451, 1380, 1262, 1067 cm$^{-1}$. $^1$H NMR (CDCl$_3$, 300 MHz) δ 1.41 (d, J=6.0 Hz, 3H), 2.22 (s, 3H), 3.69 (t, J=9.3 Hz, 1H), 4.11 (m, 1H), 4.33 (m, 2H), 4.52 (m, 1H), 4.68 (d, J=11.1 Hz, 1H), 4.86 (d, J=11.1 Hz, 1H), 5.26 (dd, J=12.3 Hz, J=3.3 Hz, 1H), 5.61 (m, 1H), 6.23 (s, 1H), 7.28 (m, 7H), 7.39 (m, 2H), 7.60 (m, 2H), 7.77 (d, J=6.6 Hz, 2H), 8.71 (s, 1H). $^{13}$C NMR (CDCl$_3$, 75 MHz) δ18.1, 21.0, 46.7, 68.4, 70.3, 70.6, 75.5, 75.6, 77.8, 94.7, 120.0, 124.9, 125.1, 127.1, 127.7, 127.8, 127.9, 128.4, 137.4, 141.1, 141.2, 142.9, 143.4, 154.0, 160.0, 169.6. MALDI-HRMS: m/z [M+Na]$^+$ calcd 684.0929, obsd 684.0939.

n-Pentenyl 3,4-O-benzyl-α-L-rhamnopyranosyide (15). Rhamnosyl trichloroacetimidate 14 (220 mg, 0.42 mmol) was azeotroped 3 times with toluene and dried for 1 h in vacuo. The compound was dissolved in dichloromethane (5 mL) and cooled to −40° C. n-Pentenol (71 mg, 85 μL, 0.83 mmol) and TMSOTf (11 mg, 9 μL, 0.04 mmol) were added, the solution was stirred for 45 min while warming to −20° C. Then it was quenched by addition of some drops of pyridine. The solvent was removed and the resulting crude product was purified by column chromatography (6:1→5:1 hexane/EtOAc) to afford 149 mg (79%) of a colorless oil. This compound (125 mg, 0.28 mmol) was dissolved in methanol (10 mL) and a solution of 0.1 M sodium methoxide (0.1 mL) was added and the solution stirred for 4 h. The solvent was removed in vacuo. The product was purified by flash column chromatography (3:1 hexane/EtOAc) to afford 109 mg (96%) of 15 as a colorless oil: $[α]_D$: −36.0 (c=0.53, CHCl$_3$), IR (thin film, CHCl$_3$): 3005, 2923, 1451, 1385, 1082 cm$^{-1}$. $^1$H NMR (CDCl$_3$, 300 MHz) δ 1.31 (d, J=6.0 Hz, 3H), 1.66 (quint., J=7.5 Hz, 2H), 2.10 (q, J=6.9 Hz, 2H), 2.48 (d, J=1.8 Hz, 1H), 3.36-3.48 (m, 2H), 3.63-3.76 (m, 2H), 3.85 (dd, J=9.0 Hz, J=3.6 Hz, 1H), 4.02 (m, 1H), 4.64 (d, J=11.1 Hz, 1H), 4.71 (s, 2H), 4.79 (s, 1H), 4.89 (d, J=10.8 Hz, 1H), 4.96-5.06 (m, 2H), 5.78 (m, 1H), 7.27-7.38 (m, 10H). $^{13}$C NMR (CDCl$_3$, 75 MHz) δ18.0, 28.7, 30.3, 66.9, 67.2, 68.6, 72.0, 75.4, 80.0, 80.1, 98.8, 114.8, 127.6, 127.7, 127.8, 127.9, 128.3, 128.4, 137.8, 137.9, 138.2. MALDI-HRMS: m/z [M+Na]$^+$ calcd 435.2142, obsd 435.2142.

n-Pentenyl 2-O-acetyl-4-O-benzyl-α-L-rhamnopyranosyl-(1→2)-3,4-O-benzyl-α-L-rhamnopyranoside (16). Compound 15 (291 mg, 0.71 mmol) and rhamnose trichloroacetimidate 13 (620 mg, 0.94 mmol) were azeotroped 3 times together with toluene and dried for 1 h in vacuo. The mixture was dissolved in dichloromethane (7 mL) and cooled to 0° C. TMSOTf (24 mg, 19 μL, 0.11 mmol) was added, the solution stirred for 1 h and quenched by addition of some drops of pyridine. The solvent was removed and the resulting crude product was purified by column chromatography (3:1 hexane/EtOAc) to afford 583 mg (91%) of a colorless oil. This compound was dissolved in dichloromethane (10 mL) and DMF (3 mL), triethylamine (0.5 mL) was added at room temperature. After 5 h the solvent was removed in vacuo. The crude product was purified by column chromatography (3:1 hexane/EtOAc) to afford 390 mg (89%) of 16 as a colorless highly viscous oil: $[α]_D$: −37.7 (c=0.35, CHCl$_3$), IR (thin film, CHCl$_3$): 2912, 1733, 1451, 1369, 1221, 1082 cm$^{-1}$. $^1$H NMR (CDCl$_3$, 300 MHz) δ 1.30 (d, J=6.3 Hz, 3H), 1.36 (d, J=6.0 Hz, 3H), 1.66 (quint., J=7.2 Hz, 2H), 2.11 (q, J=6.0 Hz, 2H), 2.16 (s, 3H), 2.21 (d, J=4.5 Hz, 1H), 3.38 (m, 2H), 3.47 (t, J=9.6 Hz, 1H), 3.66 (m, 2H), 3.87 (m, 2H), 3.96 (m, 1H), 4.20 (m, 1H), 4.61-4.74 (m, 5H), 4.88 (dd, J=14.1 Hz, J=10.8 Hz, 2H), 4.97-5.07 (m, 3H), 5.34 (m, 1H), 5.81 (m, 1H), 7.26-7.39 (m, 15H). $^{13}$C NMR (CDCl$_3$, 75 MHz) δ18.1, 18.2, 21.2, 28.7, 30.4, 66.8, 67.9, 67.9, 70.2, 72.1, 72.6, 75.0, 75.2, 75.4, 79.7, 80.2, 81.5, 98.7, 99.0, 114.9, 127.4, 127.5, 127.6, 127.8, 128.0, 128.3, 128.4, 137.9, 138.1, 138.3, 170.5. MALDI-HRMS: m/z [M+Na]$^+$ calcd 713.3296, obsd 713.3284.

As side product 57 mg (11%) of n-pentenyl 3-O-acetyl-4-O-benzyl-α-L-rhamnopyranosyl-(1→2)-3,4-O-benzyl-α-L-rhamnopyranoside (16') were obtained as a colorless highly viscous oil: $[α]_D$: −43.2 (c=0.21, CHCl$_3$), IR (thin film, CHCl$_3$): 2918, 1740, 1450, 1375, 1080 cm$^{-1}$. $^1$H NMR (CDCl$_3$, 300 MHz) δ 1.31 (d, J=6.3 Hz, 3H), 1.35 (d, J=6.0 Hz, 3H), 1.65 (quint., J=7.2 Hz, 2H), 2.09 (m, 6H), 3.37 (m, 2H), 3.47-3.60 (m, 2H), 3.63 (m, 2H), 3.86 (dd, J=12=Hz, J=2.1 Hz, 1H), 3.93 (m, 2H), 4.22 (m, 1H), 4.67-4.74 (m, 5H), 4.87 (d, J=10.8 Hz, 2H), 5.00 (m, 2H), 5.32 (dd, J=9.0 Hz, J=1.9 Hz, 1H), 5.80 (m, 1H), 7.26-7.36 (m, 15H). $^{13}$C NMR (CDCl$_3$, 75 MHz) δ18.0, 18.1, 21.3, 28.7, 30.4, 66.7, 68.0, 68.1, 69.7, 72.5, 73.6, 74.8, 75.5, 75.6, 79.1, 80.0, 80.4, 98.8, 101.2, 114.8, 127.6, 127.7, 127.7, 127.8, 128.0, 128.3, 128.3, 137.9, 138.2, 138.4, 169.7. MALDI-HRMS: m/z [M+Na]$^+$ calcd 713.3296, obsd 713.3283.

4-Methoxyphenyl 4-azido-3-O-benzyl-6-desoxy-2-O-methyl-O-D-glucopyranosyl-(1→3)-2-O-acetyl-4-O-benzyl-α-L-rhamnopyranoside (17). Compound 12 (94 mg, 0.233 mmol) and anthrose trichloroacetimidate 8 (146 mg, 0.280 mmol) were azeotroped 3 times together with toluene and dried for 30 min in vacuo. The mixture was dissolved in dichloromethane (3.5 mL) and cooled to 0° C. TMSOTf (8 mg, 7 μL, 0.035 mmol) was added, the solution stirred for 1 h and quenched by addition of some drops of pyridine. The solvent was removed and the resulting crude product was purified by column chromatography (4:1→3:1 hexane/EtOAc) to afford 160 mg (90%) of a colorless oil. This compound (265 mg, 0.348 mmol) was dissolved in dichloromethane (10 mL) and hydrazinium acetate in 2 mL of methanol was added at room temperature and stirred for 12 h. The solvent was removed by rotary evaporation and the crude product was purified by column chromatography (3:1 hexane/EtOAc) to afford 231 mg (quant.) of a colorless oil. This compound (450 mg, 0.68 mmol) was dissolved in THF (8 mL) and methyl iodide (3.84 g, 2.51 mL, 27.1 mmol). Silver (I) oxide (2.36 g, 10.2 mmol) was added as well as 5 drops of dimethyl sulfide as catalyst. The flask was wrapped in aluminium foil to exclude daylight. The mixture was stirred for 8 h. After filtration over a pad of celite to remove the silver salts a column chromatography (3:1 hexane/EtOAc) was performed to yield 335 mg (73%) of 17 as a colorless highly viscous oil: $[α]_D$: −21.7 (c=0.3, CHCl$_3$), IR (thin film, CHCl$_3$): 2934, 2110, 1742, 1601, 1507, 1248, 1093 cm$^{-1}$. $^1$H NMR (CDCl$_3$, 300 MHz) δ 1.30 (d, J=6.3 Hz, 3H), 1.34 (d, J=6.3 Hz, 3H), 2.17 (s, 3H), 3.08-3.21 (m, 3H), 3.39 (t, J=9.0 Hz, 1H), 3.16 (t, J=7.5 Hz, 1H), 3.16 (s, 3H), 3.77 (s, 3H), 3.92 (m, 1H), 4.35 (dd, J=9.6 Hz, J=3.3 Hz, 1H), 4.60 (d, J=7.5 Hz, 1H), 4.66 (d, J=10.5 Hz, 1H), 4.87 (quart., J=10.9 Hz, 2H), 5.00 (d, J=10.5 Hz, 1H), 5.32 (m, 1H), 5.34 (m, 1H), 6.82 (d, J=12.0 Hz, 1H), 6.95 (d, J=12.0 Hz, 1H), 7.26-7.44 (m, 10H). $^{13}$C NMR (CDCl$_3$, 75 MHz) δ18.1, 18.5, 21.2, 55.7, 60.7, 67.5, 68.3, 70.5, 72.2, 75.1, 75.4, 76.6, 80.5, 82.8, 84.4, 96.2, 103.0, 114.5, 117.7, 127.8, 127.9, 128.3, 128.4, 137.8, 138.0, 149.9, 154.9, 170.1. MALDI-HRMS: m/z [M+Na]$^+$ calcd 700.2841, obsd 700.2828.

4-Azido-3-O-benzyl-6-desoxy-2-O-methyl-β-D-glucopyranosyl-(1→3)-2-O-acetyl-4-O-benzyl-α-L-rhamnopyranosyl trichloroacetimidate (18). Compound 17 (125 mg, 0.185 mmol) was dissolved in a mixture of acetonitrile and water (6 mL/6 mL), cerium ammonium nitrate (354 mg, 0.646 mmol) was added in one portion and the mixture stirred for 90 min. TLC indicated complete conversion into the hemiacetal. The solution was poured into brine and the aqueous phase was extracted 2 times with EtOAc. The combined organic phases were washed 2 times with water, dried over Na$_2$SO$_4$ and concentrated. The resulting crude product was purified by column chromatography (2:1 hexane/EtOAc). The product containing fractions were concentrated and the residue dissolved in dichloromethane (2 mL) and trichloroacetonitrile (2 mL). A catalytic amount of sodium hydride (3 mg) was added, stirred for 60 min, concentrated and purified by column chromatography (3:1 hexane/EtOAc) to afford 125 mg (95%, 2 steps) of 18 as a slightly yellow oil: $[α]_D$: 3.3 (c=0.25, CHCl$_3$), IR (thin film, CHCl$_3$): 2923, 2103, 1744, 1672, 1605, 1364, 1231 cm$^{-1}$. $^1$H NMR (CDCl$_3$, 300 MHz) δ 1.23 (d, J=5.4 Hz, 3H), 1.38 (d, J=6.3 Hz, 3H), 2.17 (s, 3H), 3.06-3.17 (m, 3H), 3.38 (t, J=8.7 Hz, 1H), 3.61 (m, 1H), 3.62 (s, 3H), 3.95 (m, 1H), 4.24 (dd, J=9.6 Hz, J=3.3 Hz, 1H), 4.57 (d, J=8.1 Hz, 1H), 4.63 (d, J=10.2 Hz, 1H), 4.86 (quart., J=10.8 Hz, 2H), 4.98 (d, J=10.2 Hz, 1H), 5.32 (m, 1H), 6.19 (d, J=1.8 Hz, 1H), 7.31-7.44 (m, 10H), 8.68 (s, 1H). $^{13}$C NMR (CDCl$_3$, 75 MHz) δ18.0, 18.4, 21.0, 60.6, 67.5, 70.5, 70.7, 71.2, 75.3, 75.3, 75.6, 79.9, 82.7, 84.4, 90.9, 94.6, 103.1, 127.7, 128.0, 128.1, 128.2, 128.3, 128.4, 137.7, 137.8, 159.9, 169.6. MALDI-HRMS: m/z [M+Na]$^+$ calcd 737.1518, obsd 737.1504.

n-Pentenyl 4-azido-3-O-benzyl-6-desoxy-2-O-methyl-β-D-glucopyranosyl-(1→3)-2-O-acetyl-4-O-benzyl-α-L-rhamnopyranosyl-(1→3)-2-O-acetyl-4-O-benzyl-α-L-rhamnopyranosyl-(1→2)-3,4-O-benzyl-α-L-rhamnopyranoside (19). Disaccharide 16 (98 mg, 0.140 mmol) and disaccharide trichloroacetimidate 18 (121 mg, 0.169 mmol) were azeotroped 3 times together with toluene and dried for 30 min in vacuo. The mixture was dissolved in dichloromethane (4.5 mL) and cooled to 0° C. TMSOTf (5 mg, 4 μL, 0.021 mmol) was added, the solution stirred for 70 min and quenched by addition of some drops of pyridine. The solvent was removed and the resulting crude product was purified by column chromatography (3:1 hexane/EtOAc) to afford 154 mg (73%) of 19 as a slightly yellow highly viscous oil: [α]$_D$: −11.5 (c=0.60, CHCl$_3$), IR (thin film, CHCl$_3$): 2932, 2105, 1750, 1670, 1359 cm$^{-1}$. $^1$H NMR (CDCl$_3$, 300 MHz) δ 1.10 (d, J=6.0 Hz, 3H), 1.27 (m, 6H), 1.31 (d, J=6.0 Hz, 3H), 1.62 (m, 2H), 2.08 (m, 2H), 2.10 (s, 3H), 2.14 (s, 3H), 2.92-3.13 (m, 3H), 3.24-3.36 (m, 2H), 3.40-3.53 (m, 3H), 3.57-3.68 (m, 2H), 3.58 (s, 3H), 3.79-3.89 (m, 4H), 4.16 (t, J=3.0 Hz, 1H), 4.19 (t, J=3.0 Hz, 1H), 4.46 (d, J=7.8 Hz, 1H), 4.54-4.71 (m, 6H), 4.76-4.98 (m, 6H), 5.02 (m, 1H), 5.06 (m, 1H), 5.27 (m, 1H), 5.32 (m, 1H), 5.77 (m, 1H), 7.23-7.42 (m, 25H). $^{13}$C NMR (CDCl$_3$, 75 MHz) δ17.8, 18.0, 18.0, 18.3, 21.1, 21.2, 28.7, 30.3, 60.5, 66.8, 67.4, 67.9, 68.2, 68.6, 70.3, 71.9, 72.2, 72.2, 74.8, 75.2, 75.4, 75.5, 75.5, 75.9, 77.2, 79.4, 80.1, 80.2, 80.6, 82.6, 84.4, 98.6, 98.7, 99.1, 102.7, 114.7, 127.3, 127.4, 127.5, 127.7, 127.7, 127.9, 128.1, 128.2, 128.3, 137.8, 137.9, 138.1, 138.4, 138.4, 169.6, 169.7. MALDI-HRMS: m/z [M+Na]$^+$ calcd 1266.5720, obsd 1266.5700.

n-Pentenyl 4,6-dideoxy-4-(3-hydroxy-3-methylbutanamido)-2-O-methyl-β-D-glucopyranosyl-(1→3)-α-L-rhamnopyranosyl-(1-3)-α-L-rhamnopyranosyl-(1-2)-α-L-rhamnopyranoside (2). Tetrasaccharide 19 (37 mg, 0.029 mmol) was dissolved under an Ar atmosphere in THF (6 mL) and ammonia was condensed into the reaction vessel at −78° C. until the mixture reached a volume of about 20 mL. Small pieces of carefully washed sodium were added to the reaction vessel affording a solution with a deep blue color. After 30 min the reaction was quenched by adding some drops of methanol. Again, small pieces of sodium were added until the blue color persists for at least 30 min. The reaction was quenched by adding several mL of methanol. The dry ice bath was removed, the reaction mixture was allowed to warm to room temperature in order to evaporate the ammonia. Dowex 50-X8 acidic resin (washed and dried) was added until pH 7 was reached. The mixture was filtered, rinsed and concentrated. The crude product was purified by column chromatography using silica gel (dichloromethane/methanol 3:1). The product containing fractions were combined, concentrated and further purified by using a Sephadex column (ethanol/water 1:1). The product containing fractions were combined and concentrated affording 12 mg (60%) of a colorless film. This compound (7 mg, 0.010 mmol) was dissolved in DMF (2.5 mL) and 3-hydroxy-3-methylbutyric acid (1.8 mg, 0.015 mmol) in 0.5 mL of DMF were added. HATU (5 mg, 0.015 mmol), followed by N,N-diisopropylethylamine (2 mg, 2.5 μL, 0.015 mmol) was added yielding a slightly yellow solution. The mixture is stirred at room temperature for 2 h. ESI-MS analysis showed complete conversion (m/z 806, [M+Na]$^+$). All volatiles were removed in vacuo. The residue was purified by column chromatography using silica gel (dichloromethane/methanol 4:1) and further purified by using a Sephadex column (ethanol/water 1:1) yielding 5 mg (75%) of 2 as a colorless film: [α]$_D$: −7.9 (c=0.18, CHCl$_3$), $^1$H NMR (CD$_3$OD, 600 MHz) δ 1.21 (d, J=6.2 Hz, 3H), 1.24 (d, J=6.2 Hz, 3H), 1.25 (d, J=6.2 Hz, 3H), 1.29 (m, 9H), 1.68 (m, 2H), 2.15 (m, 2H), 2.36 (pquart., 2H), 3.02 (dd, J=9.1 Hz, J=7.9 Hz, 1H), 3.38 (m, 1H), 3.40-3.44 (m, 3H), 3.51 (t, J=9.6 Hz, 1H), 3.55-3.60 (m, 2H), 3.66 (s, 3H), 3.67 (m, 1H), 3.70-3.78 (m, 3H), 3.80 (m, 2H), 3.83 (m, 1H), 3.90 (dd, J=9.4 Hz, J=3.3 Hz, 1H), 4.05 (dd, J=3.2 Hz, J=1.9 Hz, 1H), 4.18 (dd, J=3.3 Hz, J=1.7 Hz, 1H), 4.62 (d, J=7.8 Hz, 1H), 4.77 (d, J=1.6 Hz, 1H), 4.91 (d, J=1.8 Hz, 1H), 4.96 (m, 1H), 5.03 (m, 1H), 5.05 (d, J=1.6 Hz, 1H), 5.83 (m, 1H). $^{13}$C NMR (CD$_3$OD, 150 MHz) δ18.0, 18.1, 18.2, 18.5, 29.6, 29.7, 30.0, 31.5, 49.8, 58.2, 61.2, 68.0, 70.0, 70.2, 70.6, 70.8, 71.8, 71.9, 72.2, 72.3, 73.2, 73.4, 74.4, 75.1, 79.2, 80.2, 82.0, 85.7, 100.4, 103.6, 104.0, 105.5, 115.4, 139.4, 174.7. MALDI-HRMS: m/z [M+Na]$^+$ calcd 806.3786, obsd 806.3797.

Ozonolysis of tetrasaccharide 2 and conjugation with Bovine Serum Albumine (BSA) and Keyhole Limpet Haemocyanin (KLH). Tetrasaccharide 2 (5 mg, 0.029 mmol) was dissolved in methanol (3 mL) and cooled to −78° C. Ozone gas was passed through the solution for 10 min under vigorous stirring. A pale blue solution was formed. The excess ozone was displaced with nitrogen over a period of 10 min. The blue color disappeared. Methylsulfide (0.1 mL) was added and the reaction mixture was stirred for 2 h at room temperature. Afterwards, all the volatiles were removed under a stream of nitrogen. The resulting white solid was used directly in the subsequent conjugation step. MS (ESI) experiments showed the formation of the aldehyde. The solid was dissolved in 1 mL of 0.1 M phosphate buffered saline (PBS buffer), pH 7.2. The volume was divided into two times 0.5 mL, each of them in a separate flask. In one of them 4.2 mg of BSA was added, in the other 4.2 mg of KLH. To each of the two flasks 1 mg of sodium cyanoborohydride was added and the mixtures incubated under gentle agitation at 37° C. for 48 h. After 20 h, an additional 0.5 mg of sodium cyanoborohydride was added and the incubation continued. Both mixtures were diafiltered using a Amicon Centriprep with molecular weight cut-off value of 30 000 Da with six changes of PBS at 4° C. MS (MALDI-TOF) experiments have shown seven to eight tetrasaccharide moieties attached to one BSA molecule. Larger volumes of PBS buffer in the conjugation step resulted in a smaller number of tetrasaccharide moieties attached to the protein.

Mouse Immunogenicity Studies

Mice carrying human immunoglobulin Cγ1 heavy and Cκ light chain gene segments (G. Pluschke, A. Joss, J. Marfurt, C. Daubenberger, O. Kashala, M. Zwickl, A. Stief, G. Sansig, B. Schläpfer, S. Linkert, H. van der Putten, N. Hardman, M. Schröder, J. Immunol. Meth., 1998, 215, 27-37) were immunized subcutaneously and intraperitoneally with synthetic saccharide antigens conjugated to keyhole limpet hemocyanine (KLH) formulated in ImmunEasy™ adjuvant (QIAGEN). Starting on day 0, they received at three-weekly intervals four doses of 20 μg conjugate. Blood was collected before each immunization and 2 weeks after the final injection.

Generation of Anti-Tetrasaccharide Monoclonal Antibodies (mAbs)

Three days before cell fusion, a mouse immunized with the ImmunEasy™ formulation containing the tetrasaccharide-KLH conjugate received an intravenous booster injection with 20 μg of conjugate in phosphate-buffered saline. From the sacrificed mouse the spleen was aseptically removed and a spleen cell suspension in IMDM was mixed with PAI mouse myeloma cells (Basel Institute for Immunology, Basel, Switzerland) as a fusion partner. Spleen and myeloma cells in a ratio of 1:1 were centrifuged; after the supernatant was discarded, the pellet was mixed with 1 mL pre-warmed polyethylene glycol 1500 sterile solution. After 60 sec 10 mL of culture medium were added. After 10 min cells were suspended in IMDM (Iscove's Modified Dulbecco's Medium) containing hypoxanthine, aminopterin, thymidine, and 20% fetal bovine serum (HAT) and cultured in 96-well tissue culture plates. The cells were cultured at 37° C. with 5% $CO_2$ and fed 5 days later with 100 ml of HAT-medium. Cells secreting tetrasaccharide-specific immunoglobulin (IgG) were identified by enzyme-linked immunosorbent assay (ELISA) using Immunolon 4 plates (Dynex Technologies Inc., Chantilly, Va.) coated with tetrasaccharide-BSA conjugate. Three hybridoma cell lines producing tetrasaccharide specific mAbs were identified and cloned twice by limiting dilution. Three monoclonal antibodies (mAbs), named MTA1, MTA2 and MTA3, were purified from spent culture supernatant of the three hybridoma clones by protein A affinity chromatography (HiTrap rProtein A FF, Amersham Biosciences). Purified mAbs were dialyzed against PBS with Slide-A-Lyzer Dialysis Cassette (PIERCE), aliquoted, and stored at −80° C.

Enzyme-Linked Immunosorbent Assay (ELISA)

ELISA microtiter plates Immunolon 4 (Dynex Technologies Inc., Chantilly, Va.) were coated at 4° C. overnight with 50 μL of a 10 μg/mL solution of saccharide-BSA conjugate in PBS, pH 7.2. Wells were then blocked with 5% milk powder in PBS for 1 h at room temperature followed by three washings with PBS containing 0.05% Tween-20. Plates were then incubated with two-fold serial dilutions of mouse serum or hybridoma cell supernatants in PBS containing 0.05% Tween-20 and 0.5% milk powder for 2 h at room temperature. After washing, the plates were incubated with alkaline phosphatase-conjugated goat anti-mouse IgG (γ-chain specific) antibodies (Sigma, St. Louis, Mo.) for 1 h at room temperature and then washed. Phosphatase substrate (1 mg/mL p-nitrophenyl phosphate (Sigma)) in buffer (0.14% $Na_2CO_3$, 0.3% $NaHCO_3$, 0.02% $MgCl_2$, pH 9.6) was added and incubated at room temperature. The optical density (OD) of the reaction product was recorded after appropriate time at 405 nm using a microplate reader (Titertek Multiscan MCC/340, Labsystems, Finland).

MAb Isotyping

The isotypes of the generated mAbs were determined by ELISA. ELISA microtiter plates Immunolon 4 (Dynex Technologies Inc., Chantilly, Va.) were coated at 4° C. overnight with 50 μL of a 10 μg/mL solution of tetrasaccharide-BSA conjugate in PBS. Wells were then blocked with 5% milk powder in PBS followed by three washings with PBS containing 0.05% Tween-20; then 100 μl of tested supernatants were added to different wells, which were incubated and washed again. Plates were incubated for 1 h with alkaline phosphatase-conjugated goat anti-mouse antibodies specific for IgG (Sigma); IgG1; IgGγ2b; IgG3; IgM; λ (Southern Biotech) and with alkaline phosphatase-conjugated mouse anti-human antibodies specific for IgG1 and κ (Southern Biotech). After washing, phosphatase substrate was added and incubated at room temperature. The optical density of the reaction product was recorded at 405 nm.

Immunofluorescence Assays for Detection of *Bacillus anthracis* Endospores

Endospore suspensions were added to microscope glass slides, air-dried and fixed twice with acetone. Slides were incubated in a moist chamber for 30 min at room temperature with either mouse serum diluted in PBS, hybridoma supernatants or purified mAbs diluted in PBS. After five washes with PBS, Cy3-conjugated affinity-pure $F(ab')_2$ fragment goat anti-mouse IgG antibodies (Jackson Immuno Research Laboratories, West Grove, Pa.), were added to the slides and incubated for 30 min at room temperature. Afterwards, slides were washed five times with PBS and covered with a cover slip. Antibody binding was assessed by fluorescence microscopy. The *B. anthracis* strains used for IFA were Pasteur 1, A73202 and Sterne, NCTC8234 and the *B. cereus* strain was JF1887 (ATCC9634).

Sodium Dodecyl Sulfate-Polyacrylamide Gel Electrophoresis (SDS-PAGE) and Immunoblotting Endospore suspensions were solubilized with 2× loading buffer (1.7 ml of 0.5 M Tris-HCl [pH 6.8], 2 ml of glycerol, 4.5 ml of 10% sodium dodecyl sulfate, 1 ml of β-mercaptoethanol, 0.8 ml of bromophenol blue [0.3%, wt/vol]) and heated 10 min at 95° C. before loading on the 10% SDS-PAGE. As molecular weight marker See Blue® Plus (Invitrogen) was used. Separated proteins were electrophoretically transferred to a nitrocellulose filter (Protran Nitrocellulose, BA85; Schleicher & Schuell) by semidry blotting. Blots were blocked with PBS containing 5% milk powder and 0.1% Tween 20 overnight at 4° C. Whole blots were incubated with appropriate dilutions of immune serum or mAbs in blocking buffer for 2 h at room temperature. After several washing steps, blots were incubated with goat anti-mouse IgG horseradish peroxidase conjugated Ig (BioRad Laboratories, Calif. USA) for 1 hour. After being washed again, blots were finally developed using the ECL system according to manufacturer's instructions to visualize bands.

The invention claimed is:

1. The hybridoma cell MTA1 deposited at the "Deutsche Sammlung von Mikroorganismen and Zellkulturen GmbH (DSMZ)" on Jun. 15, 2006 under the number DSM ACC2792.

2. An isolated monoclonal antibody produced by the hybridoma cell MTA1 of claim 1 against a conjugate of an oligosaccharide of formula 1 wherein R is a linker to a carrier protein and optionally comprises up to three further saccharides.

3. An assay reagent comprising an antibody according to claim 2 for the detection of *Bacillus anthracis* spores.

4. A kit comprising an antibody according to claim 2 for the detection of *B. anthracis* spores.

* * * * *